US006455673B1

(12) United States Patent
Collier

(10) Patent No.: US 6,455,673 B1
(45) Date of Patent: Sep. 24, 2002

(54) MULTI-MUTANT DIPHTHERIA TOXIN VACCINES

(75) Inventor: R. John Collier, Wellesley Hills, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 09/250,131

(22) Filed: Feb. 16, 1999

Related U.S. Application Data

(63) Continuation-in-part of application No. 08/257,781, filed on Jun. 8, 1994, now Pat. No. 5,917,017.

(51) Int. Cl.$^7$ .......................... C07K 1/00; A61K 39/00; A61K 39/08; C21P 21/04
(52) U.S. Cl. ..................... 530/350; 530/350; 424/183.1; 424/184.1; 424/185.1; 424/203.1; 424/236.1; 424/245.1; 424/239.1; 424/136.1; 424/143.1; 424/238.1; 424/178.1; 424/150.1; 435/69.1; 435/69.7; 435/29
(58) Field of Search ............................ 530/350, 391.7, 530/387.3; 424/183.1, 184.1, 185.1, 203.1, 245.1, 236.1, 239.1; 435/69.1, 69.7, 29; 426/136.1, 143.1, 150.1, 178.1, 238.1

(56) References Cited

U.S. PATENT DOCUMENTS

| 4,709,017 A | 11/1987 | Collier et al. ................ 530/350 |
| 4,950,740 A | 8/1990 | Greenfield et al. .......... 530/350 |
| 5,149,532 A | 9/1992 | Brunell ........................ 424/89 |

FOREIGN PATENT DOCUMENTS

| WO | WO92/00099 | 1/1992 | .......... A61K/39/385 |
| WO | WO93/25210 | 12/1993 | .......... A61K/31/735 |
| WO | WO95/33481 | 12/1995 | .......... A61K/30/00 |

OTHER PUBLICATIONS

Rolf et al, Infection and Immunity 1993, 61; 994–1003 Mar. 1993.*
Kaul, Pooman et al., "Roles of Glu 349 and Aspo 352 in membrane insertion and translocation by diptheria toxin"; Protein Sci., (1996), 5(4), 687–92.
Copy of International Preliminary Examination Report; May 25, 2001.
Cieplak et al.; Proc. Nat. Acad. Sci., USA 85:4667–4671; 1988.
Barbieri, et al.; "Expression of a Mutant, Full–Lengeth Form of Diphtheria Toxin in *Escherichia coli*"; Infection and Immunity 55:1647–1651; 1987.
Fisher et al.; "Construction and Expression of Plasmids Containing Mutated Diphtheria Toxin A–Chain–Coding Sequences"; Infection and Immunity 59:3562–3565; 1991.
Giannini, et al.; "The Amino–acid sequence of two non–toxic mutants of diphtheria toxin: CRM45 and CRM197"; Nucleic Acids Research 12:4063–4069; 1984.

Greenfield et al.; "Mutations in Diphtheria Toxin Separate Binding from Entry and Amplify Immunotoxin Selectivity"; Science 238:536–539; 1987.
Greenfield et al.; "Nucleotide sequence of the structural gene for diphtheria toxin carried by corynebacteriophage β"; PNAS 80:6853–6857; 1983.
Locht et al.; "Identification of amino acid residues essential for the enzymatic activities of pertussis toxin"; PNAS 86:3075–3079; 1989.
Tweten et al.; "Diphtheria Toxin, Effect of Substituting Aspartic Acid for Glutamic Acid 148 on Adp–Ribosyltyransferase Activity"; The J. of Biol. Chem. 260:10392–10394; 1985.
Maxwell et al.; "Cloning, Sequence Determination, and Expression in Transfected Cells of the Coding Sequence of the tox 176 Attenuated Diphtheria Toxin A Chain"; Mol. And Cell. Bio. 7:1576–1579; 1987.
Tang et al.; "Genetic immunization is a simple method for eliciting an immune response"; Nature 356:152–154; 1973.
Uchida et al.; "Mutation in the Structural Gene for Diphtheria Toxin carried by Temperate Phage β"; Nature New Biology 33:8–11; 1971.
Uchida et al.; "Diphtheria Toxin and Related Proteins"; The J. of Bio. Chem. 248:3838–3844; 1973.
Ward; "Diphtheria toxin: a novel cytocidal enzyme"; Trends Biochem. 12:28–30; 1987.
Wilson et al.; "Active–Site of Diphtheria Toxin: Effects of Replacing Glutamic Acid–148 with Aspartic Acid, Glutamine, or Serine"; Biochem 29:8643–8651; 1990.
Choe et al.; "The crystal structure of diphtheria toxin"; Nature 357:216–222; 1992.
Lukac et al.; "Toxoid of *Pseudomonas aeruginosa* Exotoxin A Generated by Deletion of an Active–Site Residue"; Infect. Immun. 56:3095–3098; 1988.
Killeen et al.; "Reversion of recombinant toxoids: Mutations in diphtheria toxin that partially compensate for active–site deletions"; Proc. Natl. Acad. Sci. USA 89:6207–6209; Jul. 1992.
Killeen et al.; "Conformational integrity of a recombinant toxoid of *Pseudomonas aeruginosa* exotoxin A containing a deletion of glutamic acid–553"; Biochimica et Biophysica Acta 1138:162–166; 1992.
Shen et al., "Participation of Lysine 516 and phenylalanine 530 of diphtheria toxin in receptor recognition", Journal of Biological Chemistry, 1994 vol. 269, No. 46, pp. 29077–29083, XP002153861 (abstract).
Tortorella et al., "Immunochemical analysis shows all three domains of diphtheria toxin penetrate across model membranes", J. Biol. Chem. 1995, vol. 270, No. 46, pp. 27446–27452, XP002153877 (abstract).
PCT Search Report, Mailing date Dec. 18, 2000, International Filing Date PCT/US 00/03735.
Kaul, Poonam et al., "Roles of Glu 349 and Asp 352 in membrane insertion and translocation by diphtheria toxin" Database accession No. 124:253099, XP002153862 (abstract).

* cited by examiner

*Primary Examiner*—Lynette R. F. Smith
*Assistant Examiner*—Padma Baskar
(74) *Attorney, Agent, or Firm*—Fish & Richardson P.C.

(57) ABSTRACT

Disclosed are diphtheria toxin polypeptides having multiple mutations, which render the polypeptides useful as vaccines.

7 Claims, 3 Drawing Sheets

(SEQ ID NO: 1)

```
CCGGCGTTGC GTATCCAGTG GCTACACTCA GGTTGTAATG ATTGGGATGA TGTACCTGAT    60
CTGAGAGCGA TTAAAAACTC ATTGAGGAGT AGGTCCCGAT TGGTTTTTGC TAGTGAAGCT   120
TAGCTAGCTT TCCCCATGTA ACCAATCTAT CAAAAAAGGG CATTGATTTC AGAGCACCCT   180
TATAATTAGG ATAGCTTTAC CTAATTATTT TATGAGTCCT GGTAAGGGGA TACGTTGTGA   240
GCAGAAAACT GTTTGCGTCA ATCTTAATAG GGGCGCTACT GGGGATAGGG GCCCCACCTT   300
CAGCCCATGC A                                                        311
```

|  |  |  |  |  |  |  |
|---|---|---|---|---|---|---|
| (SEQ ID NO: 2) | GGC GCT GAT GAT GTT GTT GAT TCT TCT AAA TCT TTT GTG ATG GAA AAC<br>Gly Ala Asp Asp Val Val Asp Ser Ser Lys Ser Phe Val Met Glu Asn<br>1                    5                    10                15 | 359 |

```
TTT TCT TCG TAC CAC GGG ACT AAA CCT GGT TAT GTA GAT TCC ATT CAA    407
Phe Ser Ser Tyr His Gly Thr Lys Pro Gly Tyr Val Asp Ser Ile Gln
            20                  25                  30

AAA GGT ATA CAA AAG CCA AAA TCT GGT ACA CAA GGA AAT TAT GAC GAT    455
Lys Gly Ile Gln Lys Pro Lys Ser Gly Thr Gln Gly Asn Tyr Asp Asp
        35                  40                  45

GAT TGG AAA GGG TTT TAT AGT ACC GAC AAT AAA TAC GAC GCT GCG GGA    503
Asp Trp Lys Gly Phe Tyr Ser Thr Asp Asn Lys Tyr Asp Ala Ala Gly
    50                  55                  60

TAC TCT GTA GAT AAT GAA AAC CCG CTC TCT GGA AAA GCT GGA GGC GTG    551
Tyr Ser Val Asp Asn Glu Asn Pro Leu Ser Gly Lys Ala Gly Gly Val
65                  70                  75                  80

GTC AAA GTG ACG TAT CCA GGA CTG ACG AAG GTT CTC GCA CTA AAA GTG    599
Val Lys Val Thr Tyr Pro Gly Leu Thr Lys Val Leu Ala Leu Lys Val
            85                  90                  95

GAT AAT GCC GAA ACT ATT AAG AAA GAG TTA GGT TTA AGT CTC ACT GAA    647
Asp Asn Ala Glu Thr Ile Lys Lys Glu Leu Gly Leu Ser Leu Thr Glu
        100                 105                 110

CCG TTG ATG GAG CAA GTC GGA ACG GAA GAG TTT ATC AAA AGG TTC GGT    695
Pro Leu Met Glu Gln Val Gly Thr Glu Glu Phe Ile Lys Arg Phe Gly
            115                 120                 125

GAT GGT GCT TCG CGT GTA GTG CTC AGC CTT CCC TTC GCT GAG GGG AGT    743
Asp Gly Ala Ser Arg Val Val Leu Ser Leu Pro Phe Ala Glu Gly Ser
        130                 135                 140

TCT AGC GTT GAA TAT ATT AAT AAC TGG GAA CAG GCG AAA GCG TTA AGC    791
Ser Ser Val Glu Tyr Ile Asn Asn Trp Glu Gln Ala Lys Ala Leu Ser
145                 150                 155                 160

GTA GAA CTT GAG ATT AAT TTT GAA ACC CGT GGA AAA CGT GGC CAA GAT    839
Val Glu Leu Glu Ile Asn Phe Glu Thr Arg Gly Lys Arg Gly Gln Asp
            165                 170                 175

GCG ATG TAT GAG TAT ATG GCT CAA GCC TGT GCA GGA AAT CGT GTC AGG    887
Ala Met Tyr Glu Tyr Met Ala Gln Ala Cys Ala Gly Asn Arg Val Arg
        180                 185                 190

CGA TCA GTA GGT AGC TCA TTG TCA TGC ATA AAT CTT GAT TGG GAT GTC    935
Arg Ser Val Gly Ser Ser Leu Ser Cys Ile Asn Leu Asp Trp Asp Val
            195                 200                 205
```

FIG. 1A

```
ATA AGG GAT AAA ACT AAG ACA AAG ATA GAG TCT TTG AAA GAG CAT GGC   983
Ile Arg Asp Lys Thr Lys Thr Lys Ile Glu Ser Leu Lys Glu His Gly
    210                 215                 220

CCT ATC AAA AAT AAA ATG AGC GAA AGT CCC AAT AAA ACA GTA TCT GAG  1031
Pro Ile Lys Asn Lys Met Ser Glu Ser Pro Asn Lys Thr Val Ser Glu
225                 230                 235                 240

GAA AAA GCT AAA CAA TAC CTA GAA GAA TTT CAT CAA ACG GCA TTA GAG  1079
Glu Lys Ala Lys Gln Tyr Leu Glu Glu Phe His Gln Thr Ala Leu Glu
                245                 250                 255

CAT CCT GAA TTG TCA GAA CTT AAA ACC GTT ACT GGG ACC AAT CCT GTA  1127
His Pro Glu Leu Ser Glu Leu Lys Thr Val Thr Gly Thr Asn Pro Val
            260                 265                 270

TTC GCT GGG GCT AAC TAT GCG GCG TGG GCA GTA AAC GTT GCG CAA GTT  1175
Phe Ala Gly Ala Asn Tyr Ala Ala Trp Ala Val Asn Val Ala Gln Val
        275                 280                 285

ATC GAT AGC GAA ACA GCT GAT AAT TTG GAA AAG ACA ACT GCT GCT CTT  1223
Ile Asp Ser Glu Thr Ala Asp Asn Leu Glu Lys Thr Thr Ala Ala Leu
    290                 295                 300

TCG ATA CTT CCT GGT ATC GGT AGC GTA ATG GGC ATT GCA GAC GGT GCC  1271
Ser Ile Leu Pro Gly Ile Gly Ser Val Met Gly Ile Ala Asp Gly Ala
305                 310                 315                 320

GTT CAC CAC AAT ACA GAA GAG ATA GTG GCA CAA TCA ATA GCT TTA TCG  1319
Val His His Asn Thr Glu Glu Ile Val Ala Gln Ser Ile Ala Leu Ser
                325                 330                 335

TCT TTA ATG GTT GCT CAA GCT ATT CCA TTG GTA GGA GAG CTA GTT GAT  1367
Ser Leu Met Val Ala Gln Ala Ile Pro Leu Val Gly Glu Leu Val Asp
            340                 345                 350

ATT GGT TTC GCT GCA TAT AAT TTT GTA GAG AGT ATT ATC AAT TTA TTT  1415
Ile Gly Phe Ala Ala Tyr Asn Phe Val Glu Ser Ile Ile Asn Leu Phe
        355                 360                 365

CAA GTA GTT CAT AAT TCG TAT AAT CGT CCC GCG TAT TCT CCG GGG CAT  1463
Gln Val Val His Asn Ser Tyr Asn Arg Pro Ala Tyr Ser Pro Gly His
    370                 375                 380

AAA ACG CAA CCA TTT CTT CAT GAC GGG TAT GCT GTC AGT TGG AAC ACT  1511
Lys Thr Gln Pro Phe Leu His Asp Gly Tyr Ala Val Ser Trp Asn Thr
385                 390                 395                 400

GTT GAA GAT TCG ATA ATC CGA ACT GGT TTT CAA GGG GAG AGT GGG CAC  1559
Val Glu Asp Ser Ile Ile Arg Thr Gly Phe Gln Gly Glu Ser Gly His
                405                 410                 415

GAC ATA AAA ATT ACT GCT GAA AAT ACC CCG CTT CCA ATC GCG GGT GTC  1607
Asp Ile Lys Ile Thr Ala Glu Asn Thr Pro Leu Pro Ile Ala Gly Val
            420                 425                 430

CTA CTA CCG ACT ATT CCT GGA AAG CTG GAC GTT AAT AAG TCC AAG ACT  1655
Leu Leu Pro Thr Ile Pro Gly Lys Leu Asp Val Asn Lys Ser Lys Thr
        435                 440                 445

CAT ATT TCC GTA AAT GGT CGG AAA ATA AGG ATG CGT TGC AGA GCT ATA  1703
His Ile Ser Val Asn Gly Arg Lys Ile Arg Met Arg Cys Arg Ala Ile
    450                 455                 460
```

FIG. 1B

```
GAC GGT GAT GTA ACT TTT TGT CGC CCT AAA TCT CCT GTT TAT GTT GGT  1751
Asp Gly Asp Val Thr Phe Cys Arg Pro Lys Ser Pro Val Tyr Val Gly
465             470             475             480

AAT GGT GTG CAT GCG AAT CTT CAC GTG GCA TTT CAC AGA AGC AGC TCG  1799
Asn Gly Val His Ala Asn Leu His Val Ala Phe His Arg Ser Ser Ser
            485             490             495

GAG AAA ATT CAT TCT AAT GAA ATT TCG TCG GAT TCC ATA GGC GTT CTT  1847
Glu Lys Ile His Ser Asn Glu Ile Ser Ser Asp Ser Ile Gly Val Leu
            500             505             510

GGG TAC CAG AAA ACA GTA GAT CAC ACC AAG GTT AAT TCT AAG CTA TCG  1895
Gly Tyr Gln Lys Thr Val Asp His Thr Lys Val Asn Ser Lys Leu Ser
        515             520             525

CTA TTT TTT GAA ATC AAA AGC TGAAAGGTAG TGGGGTCGTG TGCCGG         1942
Leu Phe Phe Glu Ile Lys Ser
    530             535
```

FIG. 1C

MULTI-MUTANT DIPHTHERIA TOXIN VACCINES

CROSS-REFERENCE TO RELATED APPLICATION

This application is a continuation-in-part of U.S. Ser. No. 08/257,781, filed Jun. 8, 1994, issued as U.S. Pat. No. 5,917,017 on Jun. 29, 1999.

FIELD OF THE INVENTION

This invention relates to vaccines that protect against diphtheria toxin.

BACKGROUND OF THE INVENTION

Diphtheria toxin (DT) is a protein exotoxin produced by the bacterium *Corynebacteria diphtheria*. The DT molecule is produced as a single polypeptide that is readily spliced to form two subunits linked by a disulfide bond, Fragment A (N-terminal ~f21K) and Fragment B (C-terminal ~37K), as a result of cleavage at residue 190, 192, or 193 (Moskaug, et al., *Biol Chem* 264:15709–15713, 1989; Collier et al., *Biol Chem*, 246:1496–1503, 1971). Fragment A is the catalytically active portion of DT. It is an NAD-dependent ADP-ribosyltransferase which specifically targets a protein synthesis factor termed elongation factor 2 (EF-2), thereby inactivating EF2 and shutting down protein synthesis in the cell. Fragment A consists of the diphtheria toxin C domain. Fragment A is linked to the diphtheria toxin Fragment B by a polypeptide loop. Fragment B of DT possesses a receptor-binding domain (the R domain) which recognizes and binds the toxin molecule to a particular receptor structure found on the surfaces of many types of mammalian cells. Once DT is bound to the cell via this receptor structure, the receptor/DT complex is taken up by the cell via receptor-mediated endocytosis. A second functional region on Fragment B (the T domain) acts to translocate DT across the membrane of the endocytic vesicle, releasing catalytically active Fragment A into the cytosol of the cell. A single molecule of Fragment A is sufficient to inactivate the protein synthesis machinery in a given cell.

Immunity to a bacterial toxin such as DT may be acquired naturally during the course of an infection, or artificially by injection of a detoxified form of the toxin (i.e., a toxoid) (Germanier, ed., *Bacterial Vaccines*, Academic Press, Orlando, Fla., 1984). Toxoids have traditionally been prepared by chemical modification of native toxins (e.g., with formalin or formaldehyde (Lingood et al., *Brit. J. Exp. Path.* 44:177, 1963)), rendering them nontoxic while retaining an antigenicity that protects the vaccinated animal against subsequent challenges by the natural toxin: an example of a chemically-inactivated DT is that described by Michel and Dirkx (*Biochem. Biophys. Acta* 491:286–295, 1977), in which Trp-153 of Fragment A is the modified residue.

Another method for producing toxoids is by the use of genetic techniques. Collier et al., U.S. Pat. No. 4,709,017 (herein incorporated by reference) disclosed a genetically engineered diphtheria toxin mutant that bears a deletion mutation at Glu-148 of diphtheria toxin. Glu-148 was originally identified as an active-site residue by photoaffinity labelling (Carroll et al., *Proc. Natl. Acad. Sci. USA* 81:3307, 1984; Carroll et al. *Proc. Natl. Acad. Sci. USA* 82:7237, 1985; Carroll et al., *J. Biol. Chem.* 262:8707, 1987). Substitution of Asp, Gln or Ser at this site diminishes enzymatic and cytotoxic activities by 2–3 orders of magnitude, showing that the spatial location and chemical nature of the Glu-148 side-chain greatly affects these activities (Carroll et al., *J. Biol. Chem.* 262:8707, 1987; Tweten et al., *J. Biol. Chem.* 260:10392, 1985; Douglas et al., *J. Bacteriol.* 169:4967, 1987). Similarly, Greenfield et al., U.S. Pat. No. 4,950,740 (herein incorporated by reference) disclosed genetically engineered mutant forms of DT in which the Glu-148 residue is deleted or replaced with Asn, and the Ala-158 residue is replaced with Gly. The DNA sequence and corresponding amino acid sequence of wild-type diphtheria toxin DNA are set forth in FIG. 1 (SEQ ID NOs:1 and 2, respectively).

SUMMARY OF THE INVENTION

The invention features diphtheria toxoids having multiple mutations as compared with wild-type diphtheria toxin. Thus, the invention features a polypeptide having a mutant diphtheria toxin C domain, a mutant diphtheria toxin T domain, and a mutant diphtheria toxin R domain, wherein the C domain has a mutation at Glu148, the T domain has a mutation at Glu349, and the R domain has a mutation at Lys 516 and/or Phe530 of wild-type diphtheria toxin. In various embodiments, the polypeptide includes any or all of the following mutations: Glu148Ser, Glu349Lys, Lys516Ala, and/or Phe530Ala.

The invention also features a polypeptide having a mutant diphtheria toxin C domain, a mutant T domain, and a mutant loop connecting the diphtheria toxin C and T domains, wherein the C domain has a mutation at Glu148, the T domain has a mutation at Glu349, and the loop has a mutation at Arg190, Arg192, and/or Arg193 of wild-type diphtheria toxin. In various embodiments, the polypeptide (or a mixture of polypeptides) includes any or all of the following mutations: Glu148Ser, Glu349Lys, Arg190Ser, Arg192Gly and/or Arg193Ser. In addition, all of the polypeptides of the invention bind sensitive cells with less affinity than does wild-type diphtheria toxin, and are capable of forming an immune complex with an antibody that specifically recognizes the R domain of wild-type diphtheria toxin.

These so-called "multi-mutant" diphtheria toxoids of the invention can be used as vaccines to provide immunoprotection against diphtheria toxin and against infection by *Corynebacteria diphtheriae*. One approach to vaccination utilizes live, genetically engineered microorganisms (cells or viruses) expressing mutant toxin genes. The multi-mutant toxoids of the invention, and the DNAs which encode them, carry significantly less risk of reversion than do single residue deletion mutants, and so are good candidates for use in a live, genetically engineered vaccine cell that is capable of proliferating in the vaccinee. As discussed below, acellular vaccines also are within the invention.

The invention also includes vectors (e.g., plasmids, phages and viruses) including DNA sequences encoding the diphtheria toxoid mutants described herein. Expression of a diphtheria toxoid polypeptide of the invention can be under the control of a heterologous promoter, and/or the expressed amino acids can be linked to a signal sequence. A "heterologous promoter" is a promoter region that is not identical to the promoter region found in a naturally occurring diphtheria toxin gene. The promoter region is a segment of DNA 5' to the transcription start site of a gene, to which RNA polymerase binds before initiating transcription of the gene. Nucleic acids encoding a diphtheria toxoid of the invention can be prepared as an essentially pure preparation, which is a preparation that is substantially free of other nucleic acid molecules with which a nucleic acid encoding diphtheria toxin is naturally associated in Corynebacterium. A nucleic acid encoding a diphtheria toxoid of the invention can be contained in a cell, or a homogeneous population of cells, preferably a *B. subtilis,* Bacillus Calmette-Guerin (BCG), Salmonella sp., *Vibrio cholerae, Corynebacterium diphtheriae,* Listeriae, Yersiniae, Streptococci, or *E. coli* cell. The cell is capable of expressing the diphtheria toxoid polypeptide of the invention.

Diphtheria toxoids that are "immunologically cross-reactive" possess at least one antigenic determinant in common with naturally occurring diphtheria toxin, so that they are each bound by at least one antibody with specificity for naturally occurring diphtheria toxin. A diphtheria toxoid of the invention is immunologically cross-reactive with naturally occurring diphtheria toxin and possesses at least one of the mutations described herein.

The invention includes various vaccines that can be used to immunize a mammal (e.g., a human) against progression of the disease diphtheria, and against infection by the bacterium *Corynebacterium diphtheriae.* A vaccine of the invention can include any of the various DNAs encoding a diphtheria toxoid of the invention. Alternatively, a cell or virus expressing a nucleic acid of the invention, e.g., a live vaccine cell, can be used as a vaccine. Examples of suitable cells include *B. subtilis,* BCG, Salmonella sp., *Vibrio cholerae,* Listeriae, Yersiniae, Streptococci, *Corynebacterium diphtheriae,* and *E. coli.* A "live vaccine cell" can be a naturally avirulent live microorganism, or a live microorganism with low or attenuated virulence, that expresses an immunogen. A killed-cell vaccine can also be used.

One method for manufacturing a vaccine of the invention includes culturing a cell containing DNA encoding a diphtheria toxoid of the invention under conditions permitting proliferation of the cell and expression of the DNA, the cell being one that is suitable for introduction into an animal as a live-cell vaccine. The vaccine can be used in a method of immunizing a mammal against diphtheria by introducing an immunizing amount of a vaccine of the invention into the mammal.

In an alternative method of vaccination, an acellular vaccine that includes a nucleic acid encoding a diphtheria toxoid of the invention is introduced into the mammal. For example, a DNA vaccine can be administered by biolistic transfer, a method of delivery involving coating a microprojectile with DNA encoding an immunogen of interest, and injecting the coated microprojectile directly into cells of the recipient (Tang et al., *Nature* 356:152–154, 1992; hereby incorporated by reference). The diphtheria toxoid of the invention is then expressed from the DNA to stimulate an immune response in the recipient.

The polypeptides can be made by any of a variety of conventional methods, such as by culturing any of the various cells containing a DNA encoding a diphtheria toxoid of the invention under conditions permitting expression of the DNA. Included in the invention is an isolated mutant diphtheria toxin polypeptide, an "isolated" polypeptide being one that is substantially free of cellular material, viral material, culture medium (when produced by recombinant DNA techniques), or chemical precursors or other chemicals (when chemically synthesized). Generally, the polypeptide is a substantially pure preparation, meaning that at least 50% (by weight) (e.g., at least 75%, 90%, or 99%) of the protein present in the preparation is the diphtheria toxoid polypeptide of the invention.

A vaccine against diphtheria toxin can be formulated as a composition that includes a diphtheria toxoid polypeptide of the invention and an adjuvant. Examples of adjuvants include, but are not limited to, aluminum salts, bacterial endotoxins, Bacillus Calmette-Guerin (BCG), liposomes, microspheres (i.e., microencapsulation polymers used in orally administered vaccines), and Freund's complete or incomplete adjuvant. An "adjuvant" is a substance that increases the immunogenicity of an antigen.

If desired, the diphtheria toxoid polypeptides of the invention can be covalently attached to a moiety, e.g., a polysaccharide or a second polypeptide. The moiety can serve as a carrier substance for the polypeptide or, alternatively, the diphtheria toxoid polypeptide of the invention can serve as a carrier substance for the moiety, preferably enhancing the immunogenicity of the moiety. A "carrier substance" is a substance that confers stability on, aids, and/or enhances the transport or immunogenicity of an associated molecule.

A diphtheria toxoid of the invention can also be prepared as a fusion polypeptide that includes a diphtheria toxoid polypeptide covalently linked to a second polypeptide. The fusion polypeptide can be formulated as a vaccine, which can be used to immunize a mammal (e.g., a human patient) against diphtheria toxin or infection by *Corynebacterium diphtheriae.* The fusion polypeptide can be administered directly to the mammal in a method of immunization, or it can first be combined with an adjuvant. Alternatively, the DNA encoding the fusion polypeptide can be used directly as a vaccine, or it can be incorporated into a cell (e.g., a live vaccine cell) capable of expressing the fusion polypeptide, which cell can be used as a vaccine against diphtheria toxin. A "fusion polypeptide" is a polypeptide in which a diphtheria toxoid of the invention is linked to a second polypeptide sequence, typically by expression of a genetically engineered hybrid DNA.

The mutant diphtheria toxoids of the invention can be safely administered to a mammal in the form of an acellular polypeptide, a live attenuated vaccine strain that expresses the toxoid or a nucleic acid that expresses the toxoid in the vaccinee. The diphtheria toxoids of the invention are enzymatically dysfunctional and substantially free of any risk of reversion, even in a continuously proliferating microbial host.

Other features and advantages of the invention will be apparent from the following detailed description and from the claims.

BRIEF DESCRIPTION OF THE DRAWING

FIGS. 1A–1C is a representation of the nucleotide sequence and corresponding amino acid sequence of wild-type diphtheria toxin (SEQ ID NOS:1 and 2, respectively).

DETAILED DESCRIPTION

Preparation and Analysis of Mutant Diphtheria Toxoids

Mutant diphtheria toxoids can be generated by oligonucleotide-directed mutagenesis of the diphtheria toxin gene, as described below. The mutant genes can then be expressed in *E. coli* or any other standard expression system by conventional methods, and, if desired, extracts can be assayed for NAD:EF-2 ADP-ribosyltransferase activity and diphtheria toxin-specific protein by Western blot analysis using standard methods.

EXAMPLES

Two preparations of mutant diphtheria toxin polypeptides were prepared using the following procedure. The polypeptides in these preparations were mutated as follows: (i) Glu148Ser, Glu349Lys, Lys516Ala, and Phe530Ala; and (ii)

Glu148Ser, Arg190Ser, Arg192Gly, Arg193Ser, and Glu349Lys. To produce the mutants, a gene encoding a diphtheria toxin polypeptide having the mutation Glu148Ser was further mutated to create the multi-mutant polypeptides (see, e.g., Fu et al., "Selection of Diphtheria Toxin Active-Site Mutants in Yeast" in ADP-Ribosylation in Animal Tissues, ed. Haag and Koch-Nolte, Plenum Press, N.Y.). This mutant diphtheria toxin was engineered to have a hexa-histidine tag at its carboxyl terminus in order to facilitate purification of the polypeptide by affinity chromatography. The mutant diphtheria toxin gene was cloned into the BamHI and XhoI sites of pET22b, an E. coli expression vector. To clone the diphtheria gene into the BamHI and XhoI sites of pET22b, the synthetic oligonucleotides 5'GCC GCG GAT CCG GGC CTG GAT GAT GTT G3' (SEQ ID NO:3) and 5'CGC CCG CTC GAG GCT TTT GAT TTC AAA3' (SEQ ID NO:4), respectively, were used.

Using the mutant diphtheria toxin gene as a template, additional mutations were introduced into the gene by site-directed mutagenesis as follows. To substitute Glu for Ser at position 148 of cloned diphtheria toxin gene, the mutagenic oligonucleotides 5' GGG AGT TCT AGC GTT AGC TAT ATT AAT AAC TGG3' (SEQ ID NO:5) and 5'CCA GTT ATT AAT ATA GCT AAC GCT AGA ACT CCC3' (SEQ ID NO:6) were used. To substitute Arg for Ser, Arg for Gly and Arg for Ser at position 190, 192 and 193 of cloned diphtheria toxin gene, the mutagenic oligonucleotides 5'GCA GGA AAT TCG GTC GGC TCG TCA GTA GGT AGC3' (SEQ ID NO:8) and 5'GCT ACC TAC TGA CGA GCC GAC CGA ATT TCC TGC3' (SEQ ID NO:9) were used. To substitute Glu for Lys at position 349, the mutagenic primers 5'CCA TTG GTA GGA AAA CTA GTT GAT ATT GGT3' and 5' ACC AAT ATC AAC TAG TTT TCC TAC CAA TGG3' (SEQ ID NO:10) were used. To substitute Lys for Ala at position 516, the mutagenic primers 5'GGG TAC CAG GCA ACA GTA GAT CAC3' (SEQ ID NO:11) and 5'GTG ATC TAC TGT TGC CTG GTA CCC3' (SEQ ID NO:12) were used. To substitute Phe for Ala at position 530, the mutagenic primers 5'G CTA TCG CTA GCT TTT GAA ATC3' (SEQ ID NO: 13) and 5'GAT TTC AAA AGC TAG CGA TAG C3' (SEQ ID NO:14) were used. The amplified sequences were ligated together and transformed into the E. coli strain XL1-Blue. Plasmid DNA was amplified, purified, and sequenced to confirm the presence of the mutation(s). This procedure was repeated to introduce each mutation into the multi-mutant diphtheria toxins.

Plasmid DNA containing multiple mutations in the cloned diphtheria toxin gene was transformed into BL21 cells, an E. coli host cell for expression of the diphtheria toxin. Mutant diphtheria toxins were purified from periplasmic extracts as follows. Cultures were grown in a 5 L fermentor in Luria broth containing ampicillin at 37° C. to an $OD_{600}$ of 0.8–1.0, and protein expression was induced by addition of isopropyl β-D-thiogalactopyroanoside (1 mM) for 3 hours at 28° C. Periplasmic proteins were extracted by first resuspending pelleted cells in 0.4 fermentation culture volumes of the following solution: 20% sucrose/1 mM EDTA/30 mM Tris-HCl (pH 8.0). After incubation at room temperature for 10 minutes, the mixture was centrifuged and the cell pellets were resuspended in the same volume of ice-cold 5 mM $MgSO_4$. After incubation on ice for 10 minutes, the mixture was centrifuged, and the resulting supernatant containing the desired protein was purified by affinity chromatography on a $Ni^{++}$ chelate column. The protein was then purified by gel filtration (on a Superdex 200 column) in a buffer of 20 mM Tris-HCl (pH 8.0) containing 150 mM NaCl. Proteins were purified to 95% homogeneity, as judged by SDS-PAGE. Approximately 3 mg of purified protein was obtained from one liter of fermentor culture. Proteins were stored in 20 mM Tris buffer (pH 8.0) at −20° C. until use.

Toxicity Assay

Standard methods of assaying the toxicity of diphtheria toxin mutants employ a diphtheria toxin-sensitive tissue culture cell line, which is a line of cells bearing the diphtheria toxin receptor, e.g., Vero or BSC1 cells. The cells are treated with a known amount of the mutant diphtheria toxin, with naturally occurring diphtheria toxin (as a positive control), or with a carrier protein such as bovine serum albumin (as a negative control). After incubation, viable colonies are counted to assess the extent of cell killing (see, e.g., Yamaizumi, M. et al. Cell 15:245–250, 1978). Alternatively, the extent of cell-killing can be determined by measuring the extent of inhibition of protein synthesis. After incubation with one of the diphtheria toxin samples described above, a radiolabelled amino acid (e.g., [$^{14}$C]Leu) is added to the growth medium of the cell culture, and the decline in de novo protein synthesis is measured, e.g., by scintillation counting of TCA-precipitable protein. Such methods are routine and known to one skilled in the art. The mutants described above were assayed for residual toxicity using toxin-sensitive Vero cells. The mutant polypeptides subsequently were assayed for residual toxicity by intradermal inoculation of up to 50 μg of toxoid into each guinea pig using conventional methods. The animals were observed daily for changes in activity, appetite, behavior, and appearance. The toxicity results are set forth in Table 1. Both in Vero cell cultures and following intradermal inoculation, toxoids having the mutations (i) Glu148Ser, Lys516Ala, Phe530Ala, and Glu349Lys and (ii) Arg190Ser, Arg192Gly, Arg193Ser, and Glu349Lys showed a significant reduction in toxicity, relative to the native diphtheria toxin.

Immunogenicity

After confirming that toxicity of the mutant toxoids of the invention is significantly reduced, the mutant diphtheria toxins were treated with formalin, and both formalinized and untreated diphtheria toxin samples were analyzed for immunogenicity as follows:

Guinea pigs and mice (another species that is naturally sensitive to the cell-killing effects of diphtheria toxin may be substituted) were immunized with each recombinant toxoid of the invention, separately, according to the following protocol: 1–50 μg recombinant toxoid, suspended in 250 μl of Alhydrogel (aluminum hydroxide) adjuvant, was subcutaneously injected into each of 8 guinea pigs per group. Ten groups of guinea pigs were used for each experiment over the course of one year, with 3 experiments performed per year. A 50 μl sample of the recombinant toxoid was injected into each mice. For mice, 10 animals were used per group, with 25 groups of mice used per experiment and 6 experiments performed over the course of one year. The guinea pigs and mice received two injections of the recombinant toxoid and were bled under anesthesia 2–6 times over the course of a year.

Blood samples were assayed for antitoxin antibodies by testing serial dilutions for reactivity to naturally occurring diphtheria toxin. Those animals that received high enough doses of toxoid to induce anti-toxoid formation can be challenged with wild-type diphtheria toxin, in order to determine whether the antibodies are immunoprotective. If desired, toxoids that induce a positive response in the above assay can be incorporated into live vaccines to protect against diphtheria toxin. The results of such immunogenicity assays are provided in Table 1. Appropriate live vaccine microorganisms (cells or viruses) genetically engineered to express a toxoid of the invention can be tested by injecting the vaccine into a DT sensitive animal, and, after a 2–3 month incubation period, challenging the animal with either a) a lethal dose of naturally occurring DT, or b) multiple, serially administered doses of naturally occurring DT, so as to calibrate the range of acquired immunity.

Preparation and Use of a Nucleic Acid Encoding a Diphtheria Toxoid

A DNA sequence encoding a diphtheria toxoid of the invention can be expressed by standard methods in a prokaryotic host cell. DNA encoding a diphtheria toxoid of the invention is carried on a vector and operably linked to control signals capable of effecting gene expression in the prokaryotic host. If desired, the coding sequence can contain, at its 5' end, a sequence encoding any of the known signal sequences capable of effecting secretion of the expressed protein into the periplasmic space of the host cell, thereby facilitating recovery of the protein. By way of example, a vector expressing the diphtheria toxoid of the invention, or a fusion protein including the polypeptide of the invention, can include (i) an origin of replication functional in *E. coli* derived from the plasmid pBR322; (ii) a selectable tetracycline resistance gene also derived from pBR322; (iii) a transcription termination region, e.g., the termination of the *E. coli* trp operon (placed at the end of the tetracycline resistance gene to prevent transcriptional readthrough into the trp promoter region); (iv) a transcription promoter, e.g., the trp operon promoter, or the diphtheria toxin promoter; (v) the protein coding sequence of the invention; and (vi) a transcription terminator, e.g., the T1T2 sequence from the ribosomal RNA (rrnB) locus of *E. coli*. The sequences of carrier molecules, the methods used in the synthesis of the DNA sequences, the construction of fusion genes, and the appropriate vectors and expression systems are all well known to those skilled in the art.

Similar expression systems can be designed for fusion polypeptides. For example, a nucleic acid sequence encoding the mutant diphtheria toxin can be fused to a sequence encoding a tag that facilitates purification of the fusion protein. For example, conventional recombinant DNA technology can be used to encode a hexa-histidine tag at the carboxyl terminus of the fusion protein. The hexa-histidine tag can subsequently facilitate purification of the fusion protein. These procedures are an example of, but are not limiting on, the methods of the invention.

A variety of prokaryotes, including various strains of *E. coli* can be used; however, other microbial strains can also be used, e.g., *C. diphtheriae*. Typical plasmid vectors contain replication origins, selectable markers, and control sequences derived from a species compatible with the microbial host. Commonly used prokaryotic expression control sequences (also referred to as "regulatory elements") include promoters for transcription initiation, optionally with an operator, along with ribosome binding site sequences. Promoters commonly used to direct protein expression include the beta-lactamase (penicillinase), the lactose (lac) (Chang et al., *Nature* 198:1056, 1977) and the tryptophan (trp) promoter systems (Goeddel et al., *Nucl. Acids Res.* 8:4057, 1980) as well as the lambda-derived $P_L$ promoter and N-gene ribosome binding site (Shimatake et al., *Nature* 292:128, 1981). Examples of microbial strains, vectors, and associated regulatory sequences are listed herein to illustrate, but not to limit, the invention.

Preparation and Use of a Polypeptide Vaccine

The mutant diphtheria toxoids of the invention can be expressed in any known protein expression system and then purified by standard means. Alternatively, diphtheria toxoids of the invention can be synthesized by organic chemical synthesis or produced as a biosynthesized polypeptide. Organic chemical synthesis can be performed by conventional methods of automated peptide synthesis, or by classical organic chemical techniques. The diphtheria toxoid polypeptides of the invention can be purified using conventional methods of protein isolation, e.g., methods including but not limited to precipitation, chromatography, immunoadsorption, or affinity techniques. The polypeptides can be purified from a microbial strain genetically engineered to express the diphtheria toxoid of the invention, or from a medium containing such a microbial strain. Typically, the purified diphtheria toxoid then is treated with formalin or formaldehyde to stabilize the protein, according to conventional methods.

The purified polypeptide may be combined with a suitable carrier (such as physiological saline); with an adjuvant that increases the immunogenicity of the toxoid (such as aluminum salts, bacterial endotoxins or attenuated bacterial strains (e.g., BCG or *Bordetella pertussis*), attenuated viruses, liposomes, microspheres, or Freund's complete or incomplete adjuvant)); and/or with additional toxoids or killed or attenuated vaccine organisms (to form a multivalent vaccine). Such a vaccine may then be administered to a human or non-human mammal by any acceptable method, including but not limited to oral, parenteral, transdermal and transmucosal delivery methods. Administration can be in a sustained release formulation using a biodegradable biocompatible polymer, such as a microsphere; by on-site delivery using micelles, gels or liposomes; or by transgenic modes (e.g., by biolistic administration of the DNA of the invention directly into the mammal's cells, as described by Tang et al., *Nature* 356:152–154, 1992, herein incorporated by reference). Generally, the polypeptide vaccine is administered in a dosage of 1–1,000 μg/kg body weight of the animal. Suitable dosages can readily be determined by one of ordinary skill in the art of medicine.

Preparation and Use of Live Recombinant Vaccines

Appropriate live carrier organisms include attenuated microorganisms such as BCG, Salmonella sp., *Vibrio cholerae*, Streptococci, Listeriae, and Yersiniae. The DNA of the invention can be stably transfected into such a microbial strain by standard methods (Sambrook et al., *Molecular Cloning: A Laboratory Manual*. Cold Spring Harbor Lab. Press, New York), and then would be introduced into a mammal by, for example, oral or parenteral administration. Once introduced into the patient, the bacterium would multiply and express the mutant form of diphtheria toxin within the mammal, causing the mammal to maintain a protective level of antibodies to the mutant toxin. In a similar manner, an attenuated animal virus such as adenovirus, herpes virus, vaccinia virus, polio, fowl pox, or even attenuated eukaryotic parasites such as Leishmania can be employed as the carrier organism. The mutant DNA of the invention can be incorporated by genetic engineering techniques into the genome of any appropriate virus, which is then introduced into a vaccinee by standard methods. A live vaccine of the invention can be administered at, for example, about $10^4$–$10^8$ organisms/dose, or a dose that is sufficient to stably induce protective levels of antitoxin. Optimal dosages of such a vaccine can be readily determined by one of ordinary skill in the field of vaccine technology.

Other Embodiments

Other embodiments are within the claims set forth below.

TABLE 1

| Diphtheria Construct | Vero MCD (μg) | Vero Fold-Reduction | Intra-dermal Toxicity (μg) | ID Toxicity Fold-Reduction | Toxin Neut. Ab Titer | Toxoid Neut. Ab Titer | Toxin Anti-Diphtheria IgG (μg/ml) | Toxoid Anti-Diphtheria IgG (μg/ml) |
|---|---|---|---|---|---|---|---|---|
| Native | 0.000005 | — | 0.00005 | — | 0.18 | 0.14 | — | 550 |
| ψWT | 0.009 | $2 \times 10^3$ | 0.02 | $8 \times 10^2$ | 0.14 | 0.40 | 714 | 1277 |
| Delta 148 | 2 | $4 \times 10^5$ | 50 | $1 \times 10^5$ | 0.01 | ND | 156 | ND |
| 516A/530A | 140 | $3 \times 10^7$ | 5 | $1 \times 10^4$ | 0.02 | 0.2 | 239 | 991 |
| 349K | 1000 | $2 \times 10^8$ | 10 | $2 \times 10^4$ | 0.06 | 0.2 | 832 | 778 |
| ψWT | 0.018 | $4 \times 10^3$ | ND | ND | | | | |
| 148K/51E | 2800 | $6 \times 10^8$ | 50 | $>1 \times 10^5$ | | | | |
| 190S/192G/193S/349K | 1000 | $2 \times 10^8$ | 50 | $>1 \times 10^5$ | | | | |
| 148S/516A/530A/349K | 1300 | $3 \times 10^8$ | 50 | $>1 \times 10^5$ | | | | |

What is claimed is:

1. An isolated polypeptide comprising a mutant diphtheria toxin C domain, a mutant diphtheria toxin T domain, and a mutant diphtheria toxin R domain, said C domain comprising a mutation in Glu148, said T domain comprising a mutation in Glu349, and said R domain comprising a mutation in one or both of Lys516 and Phe530 of wild-type diphtheria toxin.

2. The polypeptide of claim 1 in which the mutant C domain comprises the mutation Glu148Ser.

3. The polypeptide of claim 1 in which the mutant T domain comprises the mutation Glu349Lys.

4. The polypeptide of claim 1 in which the mutant R domain comprises the mutation Lys516Ala or the mutation Phe530Ala or both.

5. A preparation of the isolated polypeptide of claim 1 comprising a carrier.

6. The polypeptide of claim 1 in which the C domain comprises the mutation Glue148Ser, the T Domain comprises the mutation Glue349Lys, and the R domain comprises the mutations Lys516Ala and Phe530Ala.

7. A composition comprising the polypeptide of claim 1 and an adjuvant.

* * * * *

UNITED STATES PATENT AND TRADEMARK OFFICE
CERTIFICATE OF CORRECTION

PATENT NO.   : 6,455,673 B1
DATED        : September 24, 2002
INVENTOR(S)  : Dr. R. John Collier and Dr. R. John Collier It is certified that error appears in the above-identified patent and that said Letters Patent is hereby corrected as shown below:

Column 1,
Line 1, please add the following paragraph:
-- This invention was made at least in part with funding from the U.S. government (NIH grant A1 2002). The government has certain rights in this invention. --

Column 5,
Line 29, please delete "SEQ ID NO:8" and replace it with -- SEQ ID NO:7 --.
Line 30, please delete "SEQ ID NO:9" and replace it with -- SEQ ID NO:8 --.
Line 33, before the word "and" please add -- SEQ ID NO:9 --.
Line 51, please delete "5 L" and replace it with -- 5L --.

Column 7,
Lines 25, 27 and 28, please underline the text "trp".
Line 31, please underline the text "rrn".

Column 20,
Line 45, please delete "Glue148Ser" and replace it with -- Glu148Ser --.
Line 46, please delete "Glue349Lys" and replace it with -- Glu349Lys --.

Signed and Sealed this

Twelfth Day of August, 2003

JAMES E. ROGAN
*Director of the United States Patent and Trademark Office*

UNITED STATES PATENT AND TRADEMARK OFFICE
CERTIFICATE OF CORRECTION

PATENT NO.     : 6,455,673 B1
DATED          : September 24, 2002
INVENTOR(S)    : Dr. R. John Collier It is certified that error appears in the above-identified patent and that said Letters Patent is hereby corrected as shown below:

<u>Column 1,</u>
Line 1, please amend the paragraph as follows:
-- This invention was made at least in part with funding from the U.S. government (NIH grant Al 22021). The government has certain rights in this invention. --

Signed and Sealed this

Fourth Day of November, 2003

JAMES E. ROGAN
*Director of the United States Patent and Trademark Office*

SEQUENCE LISTING

<160> NUMBER OF SEQ ID NOS: 14

<210> SEQ ID NO 1
<211> LENGTH: 1942
<212> TYPE: DNA
<213> ORGANISM: Corynebacteria diphtheriae
<220> FEATURE:
<221> NAME/KEY: CDS
<222> LOCATION: (312)...(1916)

<400> SEQUENCE: 1

```
ccggcgttgc gtatccagtg gctacactca ggttgtaatg attgggatga tgtacctgat     60
ctgagagcga ttaaaaactc attgaggagt aggtcccgat tggttttgc tagtgaagct    120 tagctagctt tccccatgta accaatctat caaaaaaggg cattgatttc agagcaccct    180
tataattagg atagctttac ctaattattt tatgagtcct ggtaagggga tacgttgtga    240
gcagaaaact gtttgcgtca atcttaatag gggcgctact ggggataggg gccccacctt    300
cagcccatgc a ggc gct gat gat gtt gtt gat tct tct aaa tct ttt gtg    350
             Gly Ala Asp Asp Val Val Asp Ser Ser Lys Ser Phe Val
              1               5                  10 atg gaa aac ttt tct tcg tac cac ggg act aaa cct ggt tat gta gat    398
Met Glu Asn Phe Ser Ser Tyr His Gly Thr Lys Pro Gly Tyr Val Asp
 15                  20                  25 tcc att caa aaa ggt ata caa aag cca aaa tct ggt aca caa gga aat    446
Ser Ile Gln Lys Gly Ile Gln Lys Pro Lys Ser Gly Thr Gln Gly Asn
 30                  35                  40                  45 tat gac gat gat tgg aaa ggg ttt tat agt acc gac aat aaa tac gac    494
Tyr Asp Asp Asp Trp Lys Gly Phe Tyr Ser Thr Asp Asn Lys Tyr Asp
                 50                  55                  60 gct gcg gga tac tct gta gat aat gaa aac ccg ctc tct gga aaa gct    542
Ala Ala Gly Tyr Ser Val Asp Asn Glu Asn Pro Leu Ser Gly Lys Ala
             65                  70                  75 gga ggc gtg gtc aaa gtg acg tat cca gga ctg acg aag gtt ctc gca    590
Gly Gly Val Val Lys Val Thr Tyr Pro Gly Leu Thr Lys Val Leu Ala
         80                  85                  90 cta aaa gtg gat aat gcc gaa act att aag aaa gag tta ggt tta agt    638
Leu Lys Val Asp Asn Ala Glu Thr Ile Lys Lys Glu Leu Gly Leu Ser
     95                 100                 105 ctc act gaa ccg ttg atg gag caa gtc gga acg gaa gag ttt atc aaa    686
Leu Thr Glu Pro Leu Met Glu Gln Val Gly Thr Glu Glu Phe Ile Lys
110                 115                 120                 125 agg ttc ggt gat ggt gct tcg cgt gta gtg ctc agc ctt ccc ttc gct    734
```

```
Arg Phe Gly Asp Gly Ala Ser Arg Val Val Leu Ser Leu Pro Phe Ala
            130                 135                 140 gag ggg agt tct agc gtt gaa tat att aat aac tgg gaa cag gcg aaa       782
Glu Gly Ser Ser Ser Val Glu Tyr Ile Asn Asn Trp Glu Gln Ala Lys
                145                 150                 155 gcg tta agc gta gaa ctt gag att aat ttt gaa acc cgt gga aaa cgt       830
Ala Leu Ser Val Glu Leu Glu Ile Asn Phe Glu Thr Arg Gly Lys Arg
            160                 165                 170 ggc caa gat gcg atg tat gag tat atg gct caa gcc tgt gca gga aat       878
Gly Gln Asp Ala Met Tyr Glu Tyr Met Ala Gln Ala Cys Ala Gly Asn
        175                 180                 185 cgt gtc agg cga tca gta ggt agc tca ttg tca tgc ata aat ctt gat       926
Arg Val Arg Arg Ser Val Gly Ser Ser Leu Ser Cys Ile Asn Leu Asp
190                 195                 200                 205 tgg gat gtc ata agg gat aaa act aag aca aag ata gag tct ttg aaa       974
Trp Asp Val Ile Arg Asp Lys Thr Lys Thr Lys Ile Glu Ser Leu Lys
                210                 215                 220 gag cat ggc cct atc aaa aat aaa atg agc gaa agt ccc aat aaa aca      1022
Glu His Gly Pro Ile Lys Asn Lys Met Ser Glu Ser Pro Asn Lys Thr
                225                 230                 235 gta tct gag gaa aaa gct aaa caa tac cta gaa gaa ttt cat caa acg      1070
Val Ser Glu Glu Lys Ala Lys Gln Tyr Leu Glu Glu Phe His Gln Thr
            240                 245                 250 gca tta gag cat cct gaa ttg tca gaa ctt aaa acc gtt act ggg acc      1118
Ala Leu Glu His Pro Glu Leu Ser Glu Leu Lys Thr Val Thr Gly Thr
        255                 260                 265 aat cct gta ttc gct ggg gct aac tat gcg gcg tgg gca gta aac gtt      1166
Asn Pro Val Phe Ala Gly Ala Asn Tyr Ala Ala Trp Ala Val Asn Val
270                 275                 280                 285 gcg caa gtt atc gat agc gaa aca gct gat aat ttg gaa aag aca act      1214
Ala Gln Val Ile Asp Ser Glu Thr Ala Asp Asn Leu Glu Lys Thr Thr
                290                 295                 300 gct gct ctt tcg ata ctt cct ggt atc ggt agc gta atg ggc att gca      1262
Ala Ala Leu Ser Ile Leu Pro Gly Ile Gly Ser Val Met Gly Ile Ala
                305                 310                 315 gac ggt gcc gtt cac cac aat aca gaa gag ata gtg gca caa tca ata      1310
Asp Gly Ala Val His His Asn Thr Glu Glu Ile Val Ala Gln Ser Ile
            320                 325                 330 gct tta tcg tct tta atg gtt gct caa gct att cca ttg gta gga gag      1358
Ala Leu Ser Ser Leu Met Val Ala Gln Ala Ile Pro Leu Val Gly Glu
        335                 340                 345 cta gtt gat att ggt ttc gct gca tat aat ttt gta gag agt att atc      1406
Leu Val Asp Ile Gly Phe Ala Ala Tyr Asn Phe Val Glu Ser Ile Ile
350                 355                 360                 365 aat tta ttt caa gta gtt cat aat tcg tat aat cgt ccc gcg tat tct      1454
Asn Leu Phe Gln Val Val His Asn Ser Tyr Asn Arg Pro Ala Tyr Ser
                370                 375                 380 ccg ggg cat aaa acg caa cca ttt ctt cat gac ggg tat gct gtc agt      1502
Pro Gly His Lys Thr Gln Pro Phe Leu His Asp Gly Tyr Ala Val Ser
            385                 390                 395 tgg aac act gtt gaa gat tcg ata atc cga act ggt ttt caa ggg gag      1550
Trp Asn Thr Val Glu Asp Ser Ile Ile Arg Thr Gly Phe Gln Gly Glu
        400                 405                 410 agt ggg cac gac ata aaa att act gct gaa aat acc ccg ctt cca atc      1598
Ser Gly His Asp Ile Lys Ile Thr Ala Glu Asn Thr Pro Leu Pro Ile
        415                 420                 425 gcg ggt gtc cta cta ccg act att cct gga aag ctg gac gtt aat aag      1646
Ala Gly Val Leu Leu Pro Thr Ile Pro Gly Lys Leu Asp Val Asn Lys
430                 435                 440                 445
```

-continued

```
tcc aag act cat att tcc gta aat ggt cgg aaa ata agg atg cgt tgc      1694
Ser Lys Thr His Ile Ser Val Asn Gly Arg Lys Ile Arg Met Arg Cys
                450                 455                 460 aga gct ata gac ggt gat gta act ttt tgt cgc cct aaa tct cct gtt      1742
Arg Ala Ile Asp Gly Asp Val Thr Phe Cys Arg Pro Lys Ser Pro Val
            465                 470                 475 tat gtt ggt aat ggt gtg cat gcg aat ctt cac gtg gca ttt cac aga      1790
Tyr Val Gly Asn Gly Val His Ala Asn Leu His Val Ala Phe His Arg
        480                 485                 490 agc agc tcg gag aaa att cat tct aat gaa att tcg tcg gat tcc ata      1838
Ser Ser Ser Glu Lys Ile His Ser Asn Glu Ile Ser Ser Asp Ser Ile
    495                 500                 505 ggc gtt ctt ggg tac cag aaa aca gta gat cac acc aag gtt aat tct      1886
Gly Val Leu Gly Tyr Gln Lys Thr Val Asp His Thr Lys Val Asn Ser
510                 515                 520                 525 aag cta tcg cta ttt ttt gaa atc aaa agc tgaaaggtag tggggtcgtg        1936
Lys Leu Ser Leu Phe Phe Glu Ile Lys Ser
                530                 535 tgccgg                                                               1942

<210> SEQ ID NO 2
<211> LENGTH: 535
<212> TYPE: PRT
<213> ORGANISM: Corynebacteria diphtheriae

<400> SEQUENCE: 2

Gly Ala Asp Asp Val Val Asp Ser Ser Lys Ser Phe Val Met Glu Asn
  1               5                  10                  15

Phe Ser Ser Tyr His Gly Thr Lys Pro Gly Tyr Val Asp Ser Ile Gln
             20                  25                  30

Lys Gly Ile Gln Lys Pro Lys Ser Gly Thr Gln Gly Asn Tyr Asp Asp
         35                  40                  45

Asp Trp Lys Gly Phe Tyr Ser Thr Asp Asn Lys Tyr Asp Ala Ala Gly
     50                  55                  60

Tyr Ser Val Asp Asn Glu Asn Pro Leu Ser Gly Lys Ala Gly Gly Val
 65                  70                  75                  80

Val Lys Val Thr Tyr Pro Gly Leu Thr Lys Val Leu Ala Leu Lys Val
                 85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240
```

-continued

```
Glu Lys Ala Lys Gln Tyr Leu Glu Phe His Gln Thr Ala Leu Glu
            245                 250                 255

His Pro Glu Leu Ser Glu Leu Lys Thr Val Thr Gly Thr Asn Pro Val
        260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
                340                 345                 350

Ile Gly Phe Ala Ala Tyr Asn Phe Val Glu Ser Ile Ile Asn Leu Phe
            355                 360                 365

Gln Val Val His Asn Ser Tyr Asn Arg Pro Ala Tyr Ser Pro Gly His
        370                 375                 380

Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
                405                 410                 415

Asp Ile Lys Ile Thr Ala Glu Asn Thr Pro Leu Pro Ile Ala Gly Val
                420                 425                 430

Leu Leu Pro Thr Ile Pro Gly Lys Leu Asp Val Asn Lys Ser Lys Thr
            435                 440                 445

His Ile Ser Val Asn Gly Arg Lys Ile Arg Met Arg Cys Arg Ala Ile
        450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser
                485                 490                 495

Glu Lys Ile His Ser Asn Glu Ile Ser Ser Asp Ser Ile Gly Val Leu
            500                 505                 510

Gly Tyr Gln Lys Thr Val Asp His Thr Lys Val Asn Ser Lys Leu Ser
        515                 520                 525

Leu Phe Phe Glu Ile Lys Ser
        530                 535
```

<210> SEQ ID NO 3
<211> LENGTH: 28
<212> TYPE: DNA
<213> ORGANISM: Artificial Sequence
<220> FEATURE:
<223> OTHER INFORMATION: primer

<400> SEQUENCE: 3
gccgcggatc cgggcctgga tgatgttg                                       28

<210> SEQ ID NO 4
<211> LENGTH: 27
<212> TYPE: DNA
<213> ORGANISM: Artificial Sequence
<220> FEATURE:
<223> OTHER INFORMATION: primer

<400> SEQUENCE: 4

```
cgcccgctcg aggcttttga tttcaaa                                          27

<210> SEQ ID NO 5
<211> LENGTH: 33
<212> TYPE: DNA
<213> ORGANISM: Artificial Sequence
<220> FEATURE:
<223> OTHER INFORMATION: primer

<400> SEQUENCE: 5
gggagttcta gcgttagcta tattaataac tgg                                   33

<210> SEQ ID NO 6
<211> LENGTH: 33
<212> TYPE: DNA
<213> ORGANISM: Artificial Sequence
<220> FEATURE:
<223> OTHER INFORMATION: primer

<400> SEQUENCE: 6
ccagttatta atatagctaa cgctagaact ccc                                   33

<210> SEQ ID NO 7
<211> LENGTH: 33
<212> TYPE: DNA
<213> ORGANISM: Artificial Sequence
<220> FEATURE:
<223> OTHER INFORMATION: primer

<400> SEQUENCE: 7
gcaggaaatt cggtcggctc gtcagtaggt agc                                   33

<210> SEQ ID NO 8
<211> LENGTH: 33
<212> TYPE: DNA
<213> ORGANISM: Artificial Sequence
<220> FEATURE:
<223> OTHER INFORMATION: primer

<400> SEQUENCE: 8
gctacctact gacgagccga ccgaatttcc tgc                                   33

<210> SEQ ID NO 9
<211> LENGTH: 30
<212> TYPE: DNA
<213> ORGANISM: Artificial Sequence
<220> FEATURE:
<223> OTHER INFORMATION: primer

<400> SEQUENCE: 9
ccattggtag gaaaactagt tgatattggt                                       30

<210> SEQ ID NO 10
<211> LENGTH: 30
<212> TYPE: DNA
<213> ORGANISM: Artificial Sequence
<220> FEATURE:
<223> OTHER INFORMATION: primer

<400> SEQUENCE: 10
accaatatca actagttttc ctaccaatgg                                       30

<210> SEQ ID NO 11
<211> LENGTH: 24
<212> TYPE: DNA
<213> ORGANISM: Artificial Sequence
```

```
<220> FEATURE:
<223> OTHER INFORMATION: primer

<400> SEQUENCE: 11
gggtaccagg caacagtaga tcac                                          24

<210> SEQ ID NO 12
<211> LENGTH: 24
<212> TYPE: DNA
<213> ORGANISM: Artificial Sequence
<220> FEATURE:
<223> OTHER INFORMATION: primer

<400> SEQUENCE: 12
gtgatctact gttgcctggt accc                                          24

<210> SEQ ID NO 13
<211> LENGTH: 22
<212> TYPE: DNA
<213> ORGANISM: Artificial Sequence
<220> FEATURE:
<223> OTHER INFORMATION: primer

<400> SEQUENCE: 13
gctatcgcta gcttttgaaa tc                                            22

<210> SEQ ID NO 14
<211> LENGTH: 22
<212> TYPE: DNA
<213> ORGANISM: Artificial Sequence
<220> FEATURE:
<223> OTHER INFORMATION: primer

<400> SEQUENCE: 14
gatttcaaaa gctagcgata gc                                            22
```